US006918924B2

(12) United States Patent
Lasheras et al.

(10) Patent No.: US 6,918,924 B2
(45) Date of Patent: Jul. 19, 2005

(54) METHOD AND APPARATUS FOR REGULATING PATIENT TEMPERATURE BY IRRIGATING THE BLADDER WITH A FLUID

(75) Inventors: Juan C. Lasheras, La Jolla, CA (US); Steven A. Yon, San Diego, CA (US); Michael Magers, Encinitas, CA (US)

(73) Assignee: Innercool Therapies, Inc., San Diego, CA (US)

( * ) Notice: Subject to any disclaimer, the term of this patent is extended or adjusted under 35 U.S.C. 154(b) by 35 days.

(21) Appl. No.: 10/716,205

(22) Filed: Nov. 17, 2003

(65) Prior Publication Data

US 2004/0102826 A1 May 27, 2004

Related U.S. Application Data

(63) Continuation of application No. 09/827,010, filed on Apr. 5, 2001, now Pat. No. 6,648,906, which is a continuation-in-part of application No. 09/586,000, filed on Jun. 2, 2000, now Pat. No. 6,383,210.
(60) Provisional application No. 60/270,525, filed on Feb. 21, 2001, and provisional application No. 60/195,609, filed on Apr. 6, 2000.

(51) Int. Cl.$^7$ .................................................. A61F 7/00
(52) U.S. Cl. ........................ 607/105; 607/104; 604/27
(58) Field of Search ........................... 607/96, 104, 105, 607/113; 604/19, 27, 28, 30, 35, 43

(56) References Cited

U.S. PATENT DOCUMENTS

| 2,672,032 A | 3/1954 | Towse |
| 2,913,009 A | 11/1959 | Kuthe |
| 3,125,096 A | 3/1964 | Antiles et al. |

(Continued)

FOREIGN PATENT DOCUMENTS

| AU | 730835 B2 | 3/2001 |
| AU | 734506 B2 | 7/2001 |
| AU | 739996 B2 | 10/2001 |
| AU | 743945 B2 | 2/2002 |
| CA | 2042026 | 3/1991 |

(Continued)

OTHER PUBLICATIONS

Allen, Terry D., "Body Temperature Changes During Prostatic Resection as Related to the Temperature of the Irrigating Solution," The Journal of Urology, vol. 110, Oct. 1973, pp. 433–435.

Ambrus, "The Biphasic Nature and Temperature Dependence of the Activation of Human Plasminogen by Urokinase," Research Communications in Chemical Pathology and Pharmacology, vol. 24, No. 2, May, 1979, pp. 339–347.

Behmann, F.W., et al.; α Heat Generation Control during Artificial Hypothermia: I: Experimental Examination of the Influence of Anesthetic Depth; Pflügers Archiv, Bd. 266, S. 408–421 (1958) (German article with English translation).

(Continued)

Primary Examiner—Roy D. Gibson
(74) Attorney, Agent, or Firm—Mark D. Wieczorek

(57) ABSTRACT

A method and apparatus is provided for heating or cooling at least a selected portion of a patient's body. The method begins by inserting a catheter through the urethra and into the bladder of the patient. A heated or chilled fluid is conducted through a supply lumen of the catheter and into the bladder. The fluid is evacuated from the bladder through a return lumen of the catheter. Finally, a quantity of urine is monitored which flows out of the bladder and through the return lumen of the catheter. The rate of fluid flowing through the supply lumen of the catheter may be adjusted in a manner that is based at least in part on the monitored quantity of urine flowing out of the bladder.

16 Claims, 10 Drawing Sheets

U.S. PATENT DOCUMENTS

| | | |
|---|---|---|
| 3,425,419 A | 2/1969 | Dato |
| 3,612,175 A | 10/1971 | Ford et al. |
| 4,038,519 A | 7/1977 | Foucras |
| 4,190,033 A | 2/1980 | Foti |
| 4,298,006 A | 11/1981 | Parks |
| 4,323,071 A | 4/1982 | Simpson et al. |
| 4,602,642 A | 7/1986 | O'Hara et al. |
| 4,745,922 A | 5/1988 | Taylor |
| 4,747,826 A | 5/1988 | Sassano |
| 4,762,129 A | 8/1988 | Bonzel |
| 4,781,799 A | 11/1988 | Herbert, Jr. et al. |
| 4,820,349 A | 4/1989 | Saab |
| 4,951,677 A | 8/1990 | Crowley et al. |
| 4,964,409 A | 10/1990 | Tremulis |
| 5,000,734 A | 3/1991 | Boussignac et al. |
| 5,002,531 A | 3/1991 | Bonzel |
| 5,014,695 A | 5/1991 | Benak et al. |
| 5,024,668 A | 6/1991 | Peters et al. |
| 5,046,497 A | 9/1991 | Millar |
| 5,078,736 A | 1/1992 | Behl |
| 5,089,260 A | 2/1992 | Hunter et al. |
| 5,100,388 A | 3/1992 | Behl et al. |
| 5,106,368 A | 4/1992 | Uldall |
| RE33,911 E | 5/1992 | Samson et al. |
| 5,112,438 A | 5/1992 | Bowers |
| 5,150,706 A | 9/1992 | Cox et al. |
| 5,180,364 A | 1/1993 | Ginsburg |
| 5,183,464 A | 2/1993 | Dubrul et al. |
| 5,188,602 A | 2/1993 | Nichols |
| 5,190,539 A | 3/1993 | Fletcher et al. |
| 5,211,631 A | 5/1993 | Sheaff |
| 5,222,938 A | 6/1993 | Behl |
| 5,241,951 A | 9/1993 | Mason et al. |
| 5,250,033 A | 10/1993 | Evans et al. |
| 5,257,977 A | 11/1993 | Eshel |
| 5,267,341 A | 11/1993 | Shearin |
| 5,269,758 A | 12/1993 | Taheri |
| 5,275,611 A | 1/1994 | Behl |
| 5,306,261 A | 4/1994 | Alliger et al. |
| 5,312,360 A | 5/1994 | Behl |
| 5,330,519 A | 7/1994 | Mason et al. |
| 5,383,854 A | 1/1995 | Safar et al. |
| 5,392,766 A | 2/1995 | Masterson et al. |
| 5,395,331 A | 3/1995 | O'Neill et al. |
| 5,411,477 A | 5/1995 | Saab |
| 5,423,807 A | 6/1995 | Milder |
| 5,431,676 A | 7/1995 | Dubrul et al. |
| 5,437,673 A | 8/1995 | Baust et al. |
| 5,443,456 A | 8/1995 | Alliger et al. |
| 5,454,790 A | 10/1995 | Dubrul |
| 5,464,437 A | 11/1995 | Reid et al. |
| 5,486,208 A | 1/1996 | Ginsburg |
| 5,496,271 A | 3/1996 | Burton et al. |
| 5,531,776 A | 7/1996 | Ward et al. |
| 5,540,658 A | 7/1996 | Evans et al. |
| 5,549,559 A | 8/1996 | Eshel |
| 5,554,119 A | 9/1996 | Harrison et al. |
| 5,558,644 A | 9/1996 | Boyd et al. |
| 5,573,532 A | 11/1996 | Chang et al. |
| 5,578,008 A | 11/1996 | Hara |
| 5,584,804 A | 12/1996 | Klatz et al. |
| 5,588,438 A | 12/1996 | McKown et al. |
| 5,622,182 A | 4/1997 | Jaffe |
| 5,624,392 A | 4/1997 | Saab |
| 5,630,837 A | 5/1997 | Crowley |
| 5,643,197 A | 7/1997 | Brucker et al. |
| 5,643,335 A | 7/1997 | Reid et al. |
| 5,649,973 A | 7/1997 | Tierney et al. |
| 5,653,692 A | 8/1997 | Masterson et al. |
| 5,709,654 A | 1/1998 | Klatz et al. |
| 5,733,318 A | 3/1998 | Augustine |
| 5,733,319 A | 3/1998 | Neilson et al. |
| 5,799,661 A | 9/1998 | Boyd et al. |
| 5,800,493 A | 9/1998 | Stevens et al. |
| 5,800,516 A | 9/1998 | Fine et al. |
| 5,807,391 A | 9/1998 | Wijkamp |
| 5,820,593 A | 10/1998 | Safar et al. |
| 5,824,030 A | 10/1998 | Yang et al. |
| 5,827,222 A | 10/1998 | Klatz et al. |
| 5,827,269 A | 10/1998 | Saadat |
| 5,836,913 A | 11/1998 | Orth et al. |
| 5,837,003 A | 11/1998 | Ginsburg |
| 5,861,021 A | 1/1999 | Thome et al. |
| 5,868,735 A | 2/1999 | Lafontaine |
| 5,871,526 A | 2/1999 | Gibbs et al. |
| 5,873,835 A | 2/1999 | Hastings et al. |
| 5,879,316 A | 3/1999 | Safar et al. |
| 5,879,329 A | 3/1999 | Ginsburg |
| 5,891,094 A | 4/1999 | Masterson et al. |
| 5,899,898 A | 5/1999 | Arless et al. |
| 5,899,899 A | 5/1999 | Arless et al. |
| 5,902,268 A | 5/1999 | Saab |
| 5,906,588 A | 5/1999 | Safar et al. |
| 5,906,594 A | 5/1999 | Scarfone et al. |
| 5,906,636 A | 5/1999 | Casscells, III et al. |
| 5,913,856 A | 6/1999 | Chia et al. |
| 5,913,885 A | 6/1999 | Klatz et al. |
| 5,913,886 A | 6/1999 | Soloman |
| 5,957,917 A | 9/1999 | Doiron et al. |
| 5,957,963 A | 9/1999 | Dobak, III |
| 5,964,751 A | 10/1999 | Amplatz et al. |
| 5,968,009 A | 10/1999 | Siman |
| 5,971,979 A | 10/1999 | Joye et al. |
| 5,989,238 A | 11/1999 | Ginsburg |
| 6,007,692 A | 12/1999 | Herbert et al. |
| 6,019,783 A | 2/2000 | Philips et al. |
| 6,022,336 A | 2/2000 | Zadno-Azizi et al. |
| 6,024,740 A | 2/2000 | Lesh et al. |
| 6,033,383 A | 3/2000 | Ginsburg |
| 6,042,559 A | 3/2000 | Dobak, III |
| 6,051,019 A | 4/2000 | Dobak, III |
| 6,063,101 A | 5/2000 | Jacobsen et al. |
| 6,096,068 A | 8/2000 | Dobak, III et al. |
| 6,110,168 A | 8/2000 | Ginsburg |
| 6,126,684 A | 10/2000 | Gobin et al. |
| 6,146,411 A | 11/2000 | Noda et al. |
| 6,146,814 A | 11/2000 | Millet |
| 6,149,670 A | 11/2000 | Worthen |
| 6,149,673 A | 11/2000 | Ginsburg |
| 6,149,676 A | 11/2000 | Ginsburg |
| 6,149,677 A | 11/2000 | Dobak, III |
| 6,165,207 A | 12/2000 | Balding et al. |
| 6,194,899 B1 | 2/2001 | Ishihara et al. |
| 6,224,624 B1 | 5/2001 | Lasheras et al. |
| 6,231,594 B1 | 5/2001 | Dae |
| 6,231,595 B1 | 5/2001 | Dobak, III |
| 6,235,048 B1 | 5/2001 | Dobak, III |
| 6,238,428 B1 | 5/2001 | Werneth et al. |
| 6,245,095 B1 | 6/2001 | Dobak et al. |
| 6,251,129 B1 | 6/2001 | Dobak et al. |
| 6,251,130 B1 | 6/2001 | Dobak et al. |
| 6,254,626 B1 | 7/2001 | Dobak et al. |
| 6,261,312 B1 | 7/2001 | Dobak et al. |
| 6,264,679 B1 | 7/2001 | Keller et al. |
| 6,264,680 B1 | 7/2001 | Ash |
| 6,287,326 B1 | 9/2001 | Pecor |
| 6,290,697 B1 | 9/2001 | Tu et al. |
| 6,290,717 B1 | 9/2001 | Philips |
| 6,295,990 B1 | 10/2001 | Lewis et al. |
| 6,299,599 B1 | 10/2001 | Pham et al. |

| | | | |
|---|---|---|---|
| 6,303,156 B1 | 10/2001 | Ferrigno | |
| 6,306,161 B1 | 10/2001 | Ginsburg | |
| 6,312,452 B1 | 11/2001 | Dobak et al. | |
| 6,325,818 B1 | 12/2001 | Werneth | |
| 6,338,727 B1 | 1/2002 | Noda et al. | |
| 6,364,899 B1 | 4/2002 | Dobak, III | |
| 6,368,304 B1 | 4/2002 | Aliberto et al. | |
| 6,379,378 B1 | 4/2002 | Werneth et al. | |
| 6,383,210 B1 | 5/2002 | Magers et al. | |
| 6,393,320 B2 | 5/2002 | Lasersohn et al. | |
| 6,406,452 B1 | 6/2002 | Westerbeck | |
| 6,416,545 B1 | 7/2002 | Mikus et al. | |
| 6,602,243 B2 | 8/2003 | Noda | |
| 6,645,233 B1 | 11/2003 | Ayers et al. | |
| 6,648,906 B2 | 11/2003 | Lasheras et al. | |
| 2001/0001064 A1 | 5/2001 | Holaday | |
| 2001/0001830 A1 | 5/2001 | Dobak, III et al. | |
| 2001/0001831 A1 | 5/2001 | Dobak, III et al. | |
| 2001/0001832 A1 | 5/2001 | Dobak, III et al. | |
| 2001/0002442 A1 | 5/2001 | Dobak, III | |
| 2001/0005791 A1 | 6/2001 | Ginsburg et al. | |
| 2001/0007951 A1 | 7/2001 | Dobak, III | |
| 2001/0008975 A1 | 7/2001 | Dobak, III et al. | |
| 2001/0010011 A1 | 7/2001 | Aliberto et al. | |
| 2001/0011184 A1 | 8/2001 | Dobak, III et al. | |
| 2001/0011185 A1 | 8/2001 | Dobak, III et al. | |
| 2001/0016763 A1 | 8/2001 | Lasheras et al. | |
| 2001/0016764 A1 | 8/2001 | Dobak et al. | |
| 2001/0021865 A1 | 9/2001 | Dobak, III et al. | |
| 2001/0021866 A1 | 9/2001 | Dobak, III et al. | |
| 2001/0029394 A1 | 10/2001 | Dobak, III et al. | |
| 2001/0031946 A1 | 10/2001 | Walker et al. | |
| 2001/0032004 A1 | 10/2001 | Werneth | |
| 2001/0039440 A1 | 11/2001 | Lasheras et al. | |
| 2001/0041923 A1 | 11/2001 | Dobak, III | |
| 2001/0044644 A1 | 11/2001 | Keller et al. | |
| 2001/0047191 A1 | 11/2001 | Lasersohn et al. | |
| 2001/0047192 A1 | 11/2001 | Lasersohn et al. | |
| 2001/0047196 A1 | 11/2001 | Ginsburg et al. | |
| 2002/0002394 A1 | 1/2002 | Dobak, III | |
| 2002/0004675 A1 | 1/2002 | Lasheras | |
| 2002/0007179 A1 | 1/2002 | Dobak, III et al. | |
| 2002/0007202 A1 | 1/2002 | Dobak, III et al. | |
| 2002/0007203 A1 | 1/2002 | Gilmartin et al. | |
| 2002/0016621 A1 | 2/2002 | Werneth et al. | |
| 2002/0022823 A1 | 2/2002 | Luo et al. | |
| 2002/0026227 A1 | 2/2002 | Philips | |
| 2002/0029016 A1 | 3/2002 | Pham et al. | |
| 2002/0032430 A1 | 3/2002 | Lucetal | |
| 2002/0032474 A1 | 3/2002 | Dobak, III et al. | |
| 2002/0040717 A1 | 4/2002 | Dobak, III | |
| 2002/0045892 A1 | 4/2002 | Kramer | |
| 2002/0045925 A1 | 4/2002 | Keller et al. | |
| 2002/0049409 A1 | 4/2002 | Noda et al. | |
| 2002/0049410 A1 | 4/2002 | Noda et al. | |
| 2002/0049484 A1 | 4/2002 | Werneth et al. | |
| 2002/0077680 A1 | 6/2002 | Noda et al. | |
| 2002/0082671 A1 | 6/2002 | Magers | |
| 2003/0114835 A1 | 6/2003 | Noda | |
| 2004/0102826 A1 | 5/2004 | Lasheras et al. | |

FOREIGN PATENT DOCUMENTS

| | | | |
|---|---|---|---|
| EP | 0444184 B1 | 2/1996 | |
| WO | WO 91/03996 | 4/1991 | |
| WO | WO 91/05528 | 5/1991 | |
| WO | WO 91/16864 | 11/1991 | |
| WO | WO 92/08513 | 5/1992 | |
| WO | WO 92/20290 | 11/1992 | |
| WO | WO 92/20399 | 11/1992 | |
| WO | WO 94/20026 | 9/1994 | |
| WO | WO 95/01814 | 1/1995 | |
| WO | WO 96/00105 | 1/1996 | |
| WO | WO 96/40347 | 12/1996 | |
| WO | WO 97/01374 | 1/1997 | |
| WO | WO 97/09010 | 3/1997 | |
| WO | WO 97/25011 | 7/1997 | |
| WO | WO 97/42991 | 11/1997 | |
| WO | WO 97/43958 | 11/1997 | |
| WO | WO 98/06448 | 2/1998 | |
| WO | WO 98/26831 | 6/1998 | |
| WO | WO 98/31312 | 7/1998 | |
| WO | WO 98/50104 | 11/1998 | |
| WO | WO 95/30449 | 12/1998 | |
| WO | WO 98/57603 | 12/1998 | |
| WO | WO 99/02194 | 1/1999 | |
| WO | WO 99/37226 | 7/1999 | |
| WO | WO 99/48449 | 9/1999 | |
| WO | WO 99/66970 | 12/1999 | |
| WO | WO 99/66971 | 12/1999 | |
| WO | WO 00/02616 | 1/2000 | |
| WO | WO 01/03606 | 1/2000 | |
| WO | WO 00/06243 | 2/2000 | |
| WO | WO 00/09054 | 2/2000 | |
| WO | WO 00/10494 | 3/2000 | |
| WO | WO 00/38601 | 7/2000 | |
| WO | WO 00/40619 | 7/2000 | |
| WO | WO 00/47145 | 8/2000 | |
| WO | WO 00/48670 | 8/2000 | |
| WO | WO 00/51534 | 9/2000 | |
| WO | WO 00/53135 | 9/2000 | |
| WO | WO 00/57823 | 10/2000 | |
| WO | WO 00/62837 | 10/2000 | |
| WO | WO 00/66053 | 11/2000 | |
| WO | WO 00/69350 | 11/2000 | |
| WO | WO 00/72779 | 12/2000 | |
| WO | WO 00/72787 | 12/2000 | |
| WO | WO 01/08580 | 2/2001 | |
| WO | WO 01/10323 | 2/2001 | |
| WO | WO 01/10365 | 2/2001 | |
| WO | WO 01/12061 | 2/2001 | |
| WO | WO 01/12122 | 2/2001 | |
| WO | WO 01/13809 | 3/2001 | |
| WO | WO 01/13837 | 3/2001 | |
| WO | WO 01/17471 | 3/2001 | |
| WO | WO 01/19447 | 3/2001 | |
| WO | WO 01/26590 | 4/2001 | |
| WO | WO 01/30413 | 5/2001 | |
| WO | WO 01/41708 | 6/2001 | |
| WO | WO 01/43661 | 6/2001 | |
| WO | WO 01/49236 | 7/2001 | |
| WO | WO 01/52781 | 7/2001 | |
| WO | WO 01/56517 | 8/2001 | |
| WO | WO 01/58397 | 8/2001 | |
| WO | WO 01/64145 | 9/2001 | |
| WO | WO 01/64146 | 9/2001 | |
| WO | WO 01/66052 | 9/2001 | |
| WO | WO 01/74276 | 10/2001 | |
| WO | WO 01/76655 | 10/2001 | |
| WO | WO 01/78580 | 10/2001 | |
| WO | WO 01/87379 | 11/2001 | |
| WO | WO 01/95840 | 12/2001 | |
| WO | WO 02/07793 | 1/2002 | |
| WO | WO 02/26175 | 4/2002 | |
| WO | WO 02/26176 | 4/2002 | |
| WO | WO 02/26285 | 4/2002 | |
| WO | WO 02/26307 | 4/2002 | |
| WO | WO 02/28300 | 4/2002 | |
| WO | WO 02/36180 | 5/2002 | |
| WO | WO 02/38091 | 5/2002 | |
| WO | WO 02/47577 | 6/2002 | |
| WO | WO 02/47742 | 6/2002 | |

OTHER PUBLICATIONS

Behmann, F.W., et al.; Intravascular Cooling, a Method to Achieve Controllable Hypothermia; Pflügers Archive, vol. 263, pp. 145–165 (1956) (German article with English translation).

Behmann, F.W.; "Heat Generation Control during Artificial Hypothermia, an article about the economic problem of trembling stages"; Pflügers Archive, vol. 263, pp. 166–187 (1956) (German article with English translation).

Behmann, F.W; "Heat Generation Control during Artificial Hypothermia: II. Theoretical Examinations"; Pflügers Archiv, Bd. 266, S. 422–446 (1958) (German article with English translation).

Bigelo, "Hypothermia, Its Possible Role in Cardiac Surgery," Annals of Surgery, vol. 132, No. 5, Nov., 1959, pp. 849–866.

Bone, M.E., et al.; "Bladder Temperature as an Estimate of Body Temperature During Cardiopulmonary Bypass"; Anaesthesia; vol. 43; pp. 181–185 (1988).

Cancio, Leopoldo C. et al., "Trauma: Peritoneal Dialysis to Induce Hypothermia in a Head–Injured Patient: Case Report," Surg. Neurol. 42: 303–7, 1994.

Cheatle, "Cryostripping the Long and Short Saphenous Veins," Br. J. Surg., vol. 80, Jan. 1993.

Colvett, K. Opportunities with combined modality therapy for selective organ preservation in muscle–invasive bladder cancer. Journal of surgical oncology, vol. 63, No. 3, pp. 201–208, 1996.

Dexter, "Blood Warms as it Blows Retrograde from a Femoral Cannulation Site to the Carotid Artery During Cardiopulmonary Bypass," Perfusion, vol. 9, No. 6, Nov. 1994, pp. 393–397.

Dr. Gravenstein, Temperature, Clinical Monitoring Practices, pp. 208–210.

Elenor R. Adair, Thermoregulation IN the Presence of Microwave Fields, Handbook of Biological Effects of Electromagnetic Fields, Chapter 10, pp. 403–433.

England H.R., et al., "The Therapeutic Application of Hyperthermia in the Bladder," British Journal of Urology, pp. 849–852.

Gillinov, "Superior Cerebral Protection with Profound Hypothermia During Circulatory Arrest," Ann. Thorac. Surg., vol. 55, Nov. 1992, pp. 1432–1439.

Gomella, Leonard G., et al., "A Large Clinical Manual: Clinician's Pocket Reference", $6^{th}$ Edition, pp. 98–106, and 126–130.

Hall, R.R., et al., "Hyperthermia in the Treatment of Bladder Tumours," British journal of Urology, vol. 48, 1976, pp. 603–608.

Hayes, B., et al., "Temperature Control in Extracorporeal Circulation" 1968.

Hederer, G., et al.; "Animal Experiment Observations Regarding Cardiac Surgery under Intravascular Hypothermia"; Labgebbecjs Arch. U. Dtsch. A. Chir., Bd. 283, S. 601–625 (1957) (German article with English translation).

Higazi, "The Effect of Ultrasonic Irradiation and Temperature on Fibrinolytic Activity in Vitro," thrombosis Research, vol. 69, No. 2, Aug. 1992, pp. 251–253.

Imamaki, "Retrograde Cerebral Perfusion with Hypothermic Blood Provides Efficient Protection of the Brain," Journal of Cardiac Surgery, vol. 10, No. 4, Part 1, Jul. 1995, pp. 325–333.

Jackson, Donald, et al; "Hypothermia : IV. Study of Hypothermia Induction Time with Various Pharmacological Agents (24617)"; Proc Soc Exp Biol Med.; 100(2): 332–335 (Feb. 1959).

Jolin, "Management of a Giant Intracranial Aneurysm Using Surface–Heparinized Extracorporeal Circulation and Controlled Deep Hypothermic Low Flow Perfusion," Acta Anaesthesiologica Scandinavia, Aug. 1992, pp. 756–760.

Joseph R.C. Jansen, PhD et al., "Near Continuous Cardiac Output by Thermodilution," Journal of Clinical Monitoring, vol. 13:233–239.

Kapp, Daniel S., et al., "Bladder Cooling in Patients Treated with Regional Hyperthermia of the Pelvis Using an Annular Phased Array," International Journal Radiation Oncology Biology Physics, vol. 14, No. 6, Jun. 1988, pp. 1307–1310.

Kimoto, "Open Heart surgery Under Direct Vision with the Aid of Brain–Cooling by Irrigation," Surgery, vol. 39, No. 4, Jul. 1955, pp. 592–603.

Kubota, Yoshinobu, et al., "Treatment of Bladder Cancer with a Combination of Hyperthermia, Radiation and Bleomycin," Cancer, vol. 53, 1984, pp. 199–202.

Ludgate, C.N. et al. "Hypterthemic Perfusion of the Distended Urinary Bladder int eh Managemetn of Recurrent Transitional Cell Carcinoma," British Journal of Urology, vol. 47, 1976, pp. 841–848.

Ludgate, C.N. et al., "Hyperthermic irrigation of bladder in treatment of transitional cell carcinoma: its effectiveness in controlling persistent haematurial," Joural of the Royal Society of Medicine, vol. 72, May 1979, pp. 336–340.

Lunglmayr, G., et al. "Bladder Hyperthermia in the Treatment of Vesical Papillomatosis," International Urology and Nephrology, vol. 5, No. 1, 1973, pp. 75–84.

Maas, C. Intermittent antegrade selective cerebral perfusion during circulatory arrest for repair of aortic arch. Perfusion, vol. 12, No. 2, pp. 127–132, 1997.

Marekovic, Z., Abstract of "Renal Hypothermia in Situ by Veneous Passages: Experimental Work on Dogs," Eur Urol 6(2), 1980, 1 page.

Meden, "Effect of Hypothermia and Delayed Thrombolysis in a Rat Embolic Stroke Model," Acta Neruologica Scandinavica, Dec. 1993, pp. 91–98.

Meden, "The Influence of Body Temperature on Infarct Volume and Thromolytic Therapy in a Rat embolic Stroke Model," Brain Research, vol. 647, Feb. 1994, pp. 131–138.

Milleret, Abstract of "Cryosclerosis of the Saphenous Veins in Varicose Reflux in the Obese and Elderly," Phlebologie, vol. 34, No. 4, Oct. 1981, one page.

Milleret, Rene, "La–cryo–chirurgie danes les varices des mimbres inferieurs," Angiologie, Supplement No. 110.

Monga, M. et al., "Effect of irrigating fluid on perioperative temperature regulation during transurethral prostatectomy," Abstract, Eur Urol 1996, vol. 29(1):26–28.

Netto, I.C.V. et al., "Marked Hyperthermia Effect on Male Canine Urinary Bladder," Urology, vol. 1, No. 4, Apr. 1973, pp. 347–350.

Nissenkorn, I. et al., "Temperature Measurements and Histology of the Canine Prostate During Transurethral Hyperthermia," The Journal of Urology, vol. 149, Jun. 1993, pp. 1613–1616.

Parkins, "Brain cooling in the Prevention of brain Damage During Periods of Circulatory Occlusion in Dogs," Annals of Surgery, vol. 140, No. 3, Apr. 1954, pp. 284–289.

Piepgras, "Rapid Active Internal Core Cooling for Induction of Moderate Hypothermia in Head Injury by Use of an Extracorporeal Heat Exchanger," Neurosurgery, vol. 42, No. 2, Feb. 1998, pp. 311–318.

Plattner, Olga, et al., "Efficiacy of Intraoperative Cooling Methods," *Anesthesiology*, 87:1089–95, 1997.

Pond, Harry S. et al., "The Effect of Moderate Hypothermia on Canine Bladder". *Investigative Urology*, vol. 7, No. 6, May 1970, pp 460–466.

Rijken, "Plasminogen Activation at Low Temperatures in Plasma Samples Containing Therapeutic Concentrations of Tissue–Type Plasminogen Activator of Other Thrombolytic Agents," Place of Publication Unknown, Oct. 1989, pp. 47–52.

Roehrorn, Claus G., et al., "Temperature Mapping in the Canine Prostate During Transurethrally–Applied Local Microwave Hyperthermia," *The Prostate*, vol. 20, 1992, pp. 97–104.

Schwartz, "Cerebral Blood Flow During Low–Flow Hypothermic Cardiopulmonary Bypass in Baboons," Anesthesiology, vol. 81, No. 4, Jun. 1994, pp. 959–964.

Schwartz, "Selective Cerebral Hypothermia by Means of Transfemoral Intenral Carotid Artery Catheterization," Radiology, vol. 201, No. 2, May 1996, pp. 571–572.

Schwartz, A.E. et al., "Isolated cerebral hypothermia by single carotid artery perfusion of extracorporeally cooled blood in baboons," Neurosurgery 39(3): 577–582.

Sessler, "Temperature–Monitoring and Thermal Management Guidelines," Anesthesiology 1998; 89:1298–1300.

Shiraki, K. et al., "Esophageal and Tympanic Temperature Responses to Core Blood Temperature Changes During Hyperthermia," The American Physiological Society, 1986, pp. 98–102.

Steen, "The Detrimental Effects of Prolonged Hypothermia and Rewarming in the Dog," Anesthesiology, vol. 52, No.3, Aug. 1979. pp. 224–230.

Vandam, "Hypothermia", The New England Journal of Medicine, Sep. 1959, pp. 546–553.

White, "Cerebral Hypothermia and Circulatory Arrest," Mayo Clinic Proceedings, vol. 53, Jul. 1978, pp. 450–458.

Yenari, "Thrombolysis with Tissue Plasminogen Activator (TPA) is Temperature Dependent," Thrombosis Research, vol. 77, No. 5, Jul. 1994, pp. 475–481.

Yoshihara, "Changes in Coagulation and Fibrinolysis Occurring in Dogs During Hypothermia," Thrombosis Research, vol. 37, No. 4, Aug. 1984, pp. 503–512.

Zarins, "Circulation in Profound Hypothermia," Journal of Surgical Research, vol. 14, No. 2, Nov. 1972, pp. 97–104.

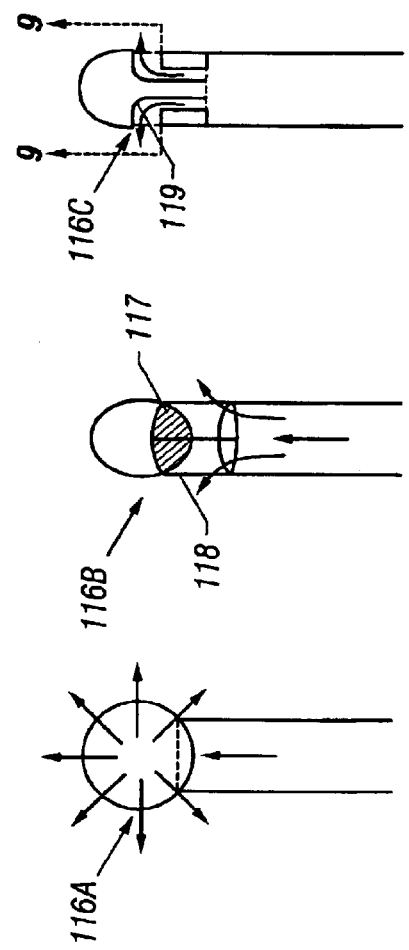
FIG. 10
FIG. 11
FIG. 12
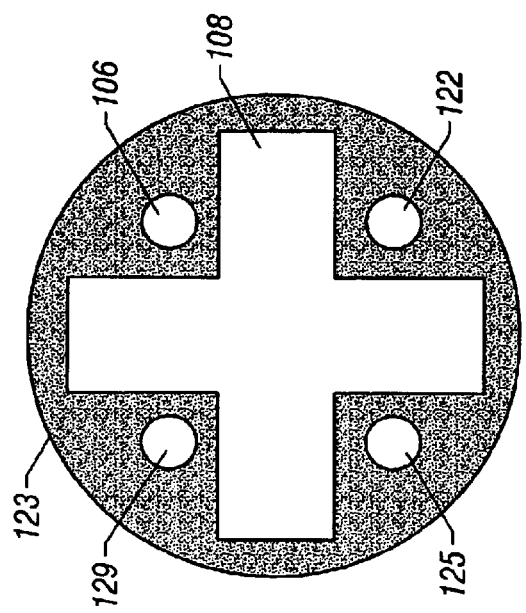
FIG. 9

METHOD AND APPARATUS FOR REGULATING PATIENT TEMPERATURE BY IRRIGATING THE BLADDER WITH A FLUID

RELATED APPLICATIONS

This application is a continuation of U.S. patent application Ser. No. 09/827,010, filed on Apr. 5, 2001 now U.S. Pat. No. 6,648,906, entitled "Method And Apparatus For Regulating Patient Temperature By Irrigating The Bladder With A Fluid" which is a continuation-in-part of U.S. patent application Ser. No. 09/586,000, filed on Jun. 2, 2000 now U.S. Pat. No. 6,383,210, entitled "Method For Determining The Effective Thermal Mass Of A Body Or Organ Using A Cooling Catheter," and claims priority to U.S. Provisional Patent Application Ser. No. 60/195,609, filed Apr. 6, 2000, entitled "Bladder Cooling for Total Body Therapeutic Hypothermia", and U.S. Provisional Patent Application Ser. No. 60/270,525, filed Feb. 21, 2001, entitled "Method And Apparatus For Regulating Patient Temperature By Irrigating The Bladder With A Fluid", all of which are incorporated herein by reference.

BACKGROUND OF THE INVENTION

I. Field of the Invention

The present invention relates generally to the modification and control of the temperature of the body. More particularly, the invention relates to a method for controlling body temperature by irrigating the bladder with a working fluid.

II. Description of the Related Art

Organs in the human body, such as the brain, kidney and heart, are maintained at a constant temperature of approximately 37° C. Hypothermia can be clinically defined as a core body temperature of 35° C. or less. Hypothermia is sometimes characterized further according to its severity. A body core temperature in the range of 33° C. to 35° C. is described as mild hypothermia. A body temperature of 28° C. to 32° C. is described as moderate hypothermia. A body core temperature in the range of 24° C. to 28° C. is described as severe hypothermia.

Patients may require pre or post-operative cooling for a variety of reasons, including, for example, treatment of a malignant hypothermia crisis and induction of therapeutic hypothermia for neurosurgery.

Catheters have been developed which are inserted into the bloodstream of the patient in order to induce total body hypothermia. For example, U.S. Pat. No. 3,425,419 to Dato describes a method and apparatus of lowering and raising the temperature of the human body. The Dato invention is directed towards a method of inducing moderate hypothermia in a patient using a metallic catheter. The metallic catheter has an inner passageway through which a fluid, such as water, can be circulated. The catheter is inserted through the femoral vein and then through the inferior vena cava as far as the right atrium and the superior vena cava. The Dato catheter has an elongated cylindrical shape and is constructed from stainless steel.

Other less cumbersome catheters have been developed to provide cooling intravascularly. For example, a heat transfer element such as disclosed in U.S. Pat. No. 6,096,068, incorporated herein by reference in its entirety, may be placed in the feeding artery of an organ to absorb or deliver the heat from or to the blood flowing into the organ. The transfer of heat may cause either a cooling or a heating of the selected organ. The heat transfer element is small enough to fit within the feeding artery while still allowing a sufficient blood flow to reach the organ in order to avoid ischemic organ damage. By placing the heat transfer element within the feeding artery of an organ, the temperature of the organ can be controlled with less of an effect on the temperature of the remaining parts of the body. A similar heat transfer device, which is employed for whole body cooling and is disposed in the venous vasculature, is disclosed in U.S. application Ser. No. 09/373,112, also incorporated by reference in its entirety.

While the previously mentioned techniques provide significant thermal control, they require the insertion of a catheter into the vascular system to induce heat transfer between the catheter and the blood stream. This is a relatively invasive procedure, which has an associated level of risk.

Accordingly, it would be desirable to provide an effective, less invasive method and apparatus for heating or cooling all or part of a patient's body. It would also be desirable to provide an effective, less invasive method and apparatus for heating or cooling all or part of a patient's body that could be employed in emergency situations, such as on an ambulance.

SUMMARY OF THE INVENTION

The present invention provides a method and apparatus for heating or cooling at least a selected portion of a patient's body. The method begins by inserting a catheter through the urethra and into the bladder of the patient. A heated or chilled fluid is conducted through a supply lumen of the catheter and into the bladder. The fluid is evacuated from the bladder through a return lumen of the catheter. Finally, a quantity of urine is monitored which flows out of the bladder and through the return lumen of the catheter.

In accordance with one aspect of the invention, the rate of fluid flowing through the supply lumen of the catheter is adjusted in a manner that is based at least in part on the monitored quantity of urine flowing out of the bladder.

In accordance with another aspect of the invention, the fluid is conducted into the supply lumen at a substantially constant flow rate, or alternatively, at a periodically interrupted rate. In one particular embodiment of the invention, the flow rate is less than a flow rate that would substantially prevent fluid from flowing from the kidneys to the bladder. In this or another embodiment of the invention, the flow rate of fluid conducted into the supply lumen is substantially equal to a flow rate of fluid being evacuated from the bladder.

In accordance with another aspect of the invention, the pressure of the fluid flowing into the supply lumen is monitored. The pressure of the fluid flowing through the return lumen may be monitored as well.

In accordance with yet another aspect of the invention, a temperature differential is monitored between the fluid conducted into the supply lumen and the fluid flowing through the return lumen.

BRIEF DESCRIPTION OF THE DRAWINGS

FIG. 9 shows a cross-section of the catheter at a point proximal of the balloon.

FIGS. 10–12 show various optional dispersion tips located on the supply orifice of the catheter for distributing fluid throughout the bladder.

DETAILED DESCRIPTION OF THE INVENTION

The present invention provides a relatively non-intrusive method and apparatus for heating or cooling all or part of a patient's body. The invention achieves this result by circulating a heat transfer fluid through the patient's bladder 11 (see FIG. 3). Heat transfer via the bladder 11 is advantageous because the bladder 11 is located in the abdominal cavity, surrounded by a variety of organs, and in addition the bladder walls are highly perfused with blood. Further, the abdominal cavity volume includes a substantial portion of the high blood flow vessels the aorta 17 and the inferior vena cava 19. The fluid absorbs heat from or delivers heat through the wall of the bladder 11 and into the abdominal cavity and the arterial and venous vessels populating this area, thereby regulating the temperature of a patient's whole body or one or more selected organs. In particular, the bladder 11 is supplied with blood by the superior, middle and inferior vesical arteries, which arise from the anterior trunk of the intereal iliac artery. As a result, cooling of the internal organs and a considerable amount of blood can be accomplished without the invasive step of inserting a catheter directly into the vascular system.

In addition, for surgeries requiring more than about two hours to perform, insertion of a catheter into the bladder to monitor urine output is a common procedure. Such urethral catheters are commonly termed "Foley" catheters. A common Foley-type catheter may be the basis for the design and construction of a catheter according to the invention. As described below, however, significant modifications may be made to a common Foley catheter in order to make the same optimum for the present methods.

Figure 1:
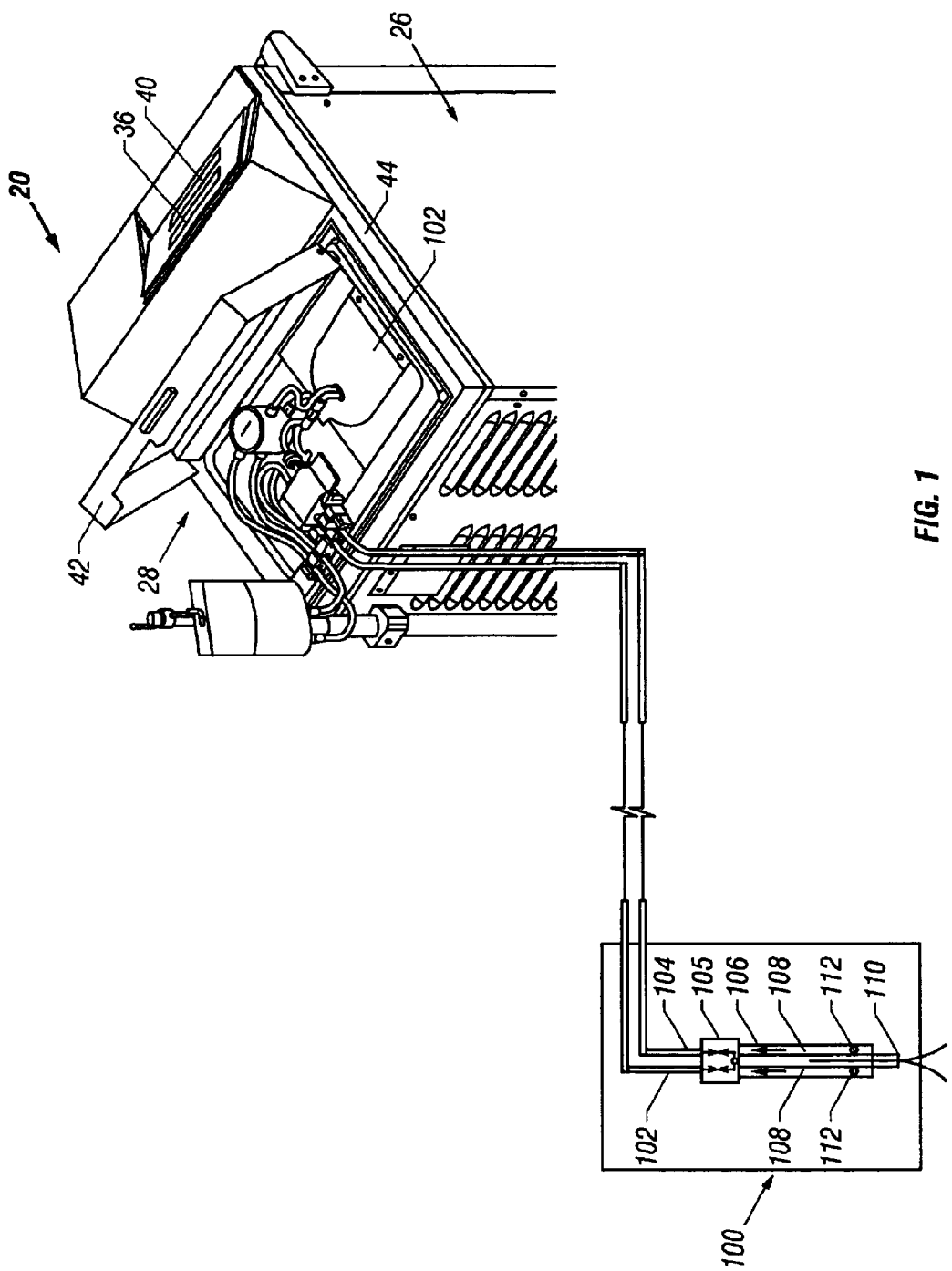
FIG. 1 is a partially perspective and partially schematic view of a catheter system including a circulation set constructed in accordance with the present invention.

FIG. 1 shows one embodiment of the bladder thermal control system 20 constructed in accordance with the present invention. The system includes a catheter 100, control system 26, and a circulation set 28 partially housed by the control unit system 26. The control system 26 may be equipped with an output display 36 and input keys 40 to facilitate user interaction with the control system 26. While FIG. 1 shows a fairly large and relatively complex control system 26, the complexity of the same depends on the application to which the same is put. For example, for a rewarming application, the control system 26 may be a simple Mallinkrodt Blood and Fluid Warmer, as manufactured by Mallinkrodt Medical of St. Louis, Mo.

Alternatively, for certain applications, such as rewarming or maintaining normothermia during a surgery or other procedure, the nature of the heat exchanger used within the control system may be simple, such as a simple resistive heat exchanger or thermo-electric heat exchanger.

The catheter 100, which may employ a design similar to that of a Foley catheter, for example, is configured for insertion into the urethra. The proximal end of the catheter 100 includes a manifold 105 having an inlet port 102 and an outlet port 104 on its proximal end. A supply lumen 106 and a return lumen 108 are connected to a port located on the distal end of the manifold 105. At the catheter's distal end the supply and return lumens 106 and 108 respectively terminate in supply and return orifices 110 and 112. The catheter may have a diameter of, e.g., 18 F or another size as dictated by the requirements of the user.

Figure 3:
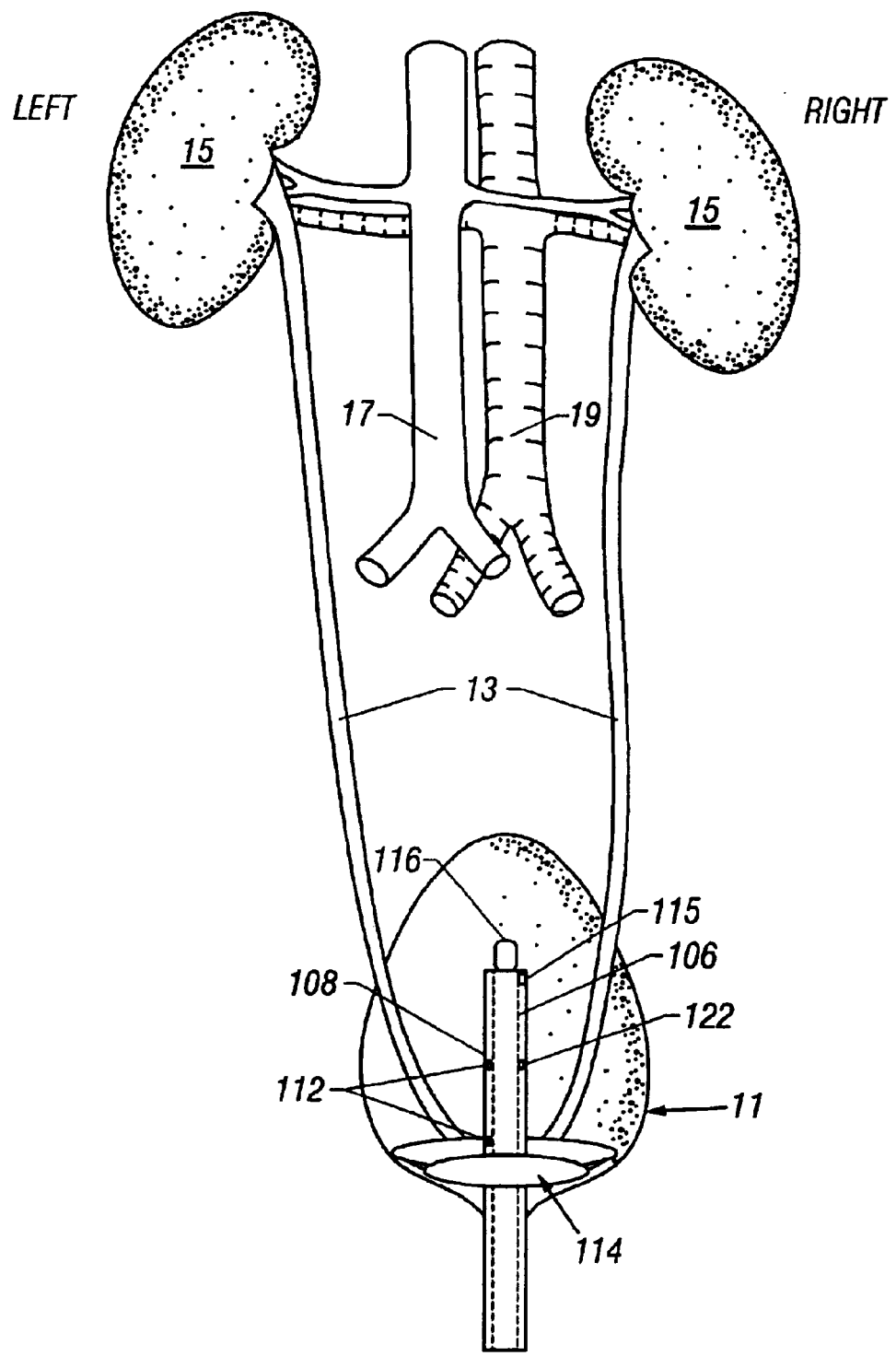
FIG. 3 shows the distal end of the catheter depicted in FIGS. 1 and 2 inserted into the bladder.

The supply orifice 110 may include an optional dispersion tip. In FIG. 3, both a supply orifice 115 and a dispersion tip 116 are shown, although in practice typically only one or the other would be used. The supply orifice 110 may cause the fluid to emerge in a direction parallel to the axis of the catheter (supply orifice 110) or perpendicular to the same (supply orifice 115). These aspects are discussed in more detail below in connection with FIGS. 4–8.

Whether a dispersion tip is used or not, the distal tip or supply orifice of the catheter may be made of a very soft material so as to minimize tissue damage of the urethra upon insertion. The same may be coated with various materials to minimize deleterious coating of undesired biological materials on the tip during or after insertion.

The supply and return lumens 106 and 108 may be formed from a pair of concentric flexible tubes so that the supply lumen 106 may be concentrically located within the annular return lumen 108. Of course, the same may also be non-coaxial as dictated by the requirements of the user. As shown in more detail in FIG. 3, when the catheter 100 is properly inserted into the urethra its distal end is located in the bladder. Fluid is conducted into the bladder from the supply lumen 106 via supply orifice 110. Fluid is conducted out of the bladder 11 via at least one return orifice 112 and into return lumen or lumens 108. As FIG. 3 indicates, in some embodiments of the invention the supply orifice 110 is spatially separated from the return orifices 112 so that fluid has an opportunity to thoroughly irrigate the bladder 11 before returning through the return orifice 112.

As in a conventional Foley catheter, the catheter 100 may include a balloon 14 (see FIGS. 3 and 4) near its tip to prevent its expulsion from the urethra. The balloon 14 may also serve the purpose of anchoring the catheter against movement caused by a pulsating working fluid supply, as may be the case if certain types of pumps are employed to drive the working fluid. The balloon 14 may be inflated by a single inflation lumen, a dual inflation lumen, or other such lumen as is known.

Figure 2:
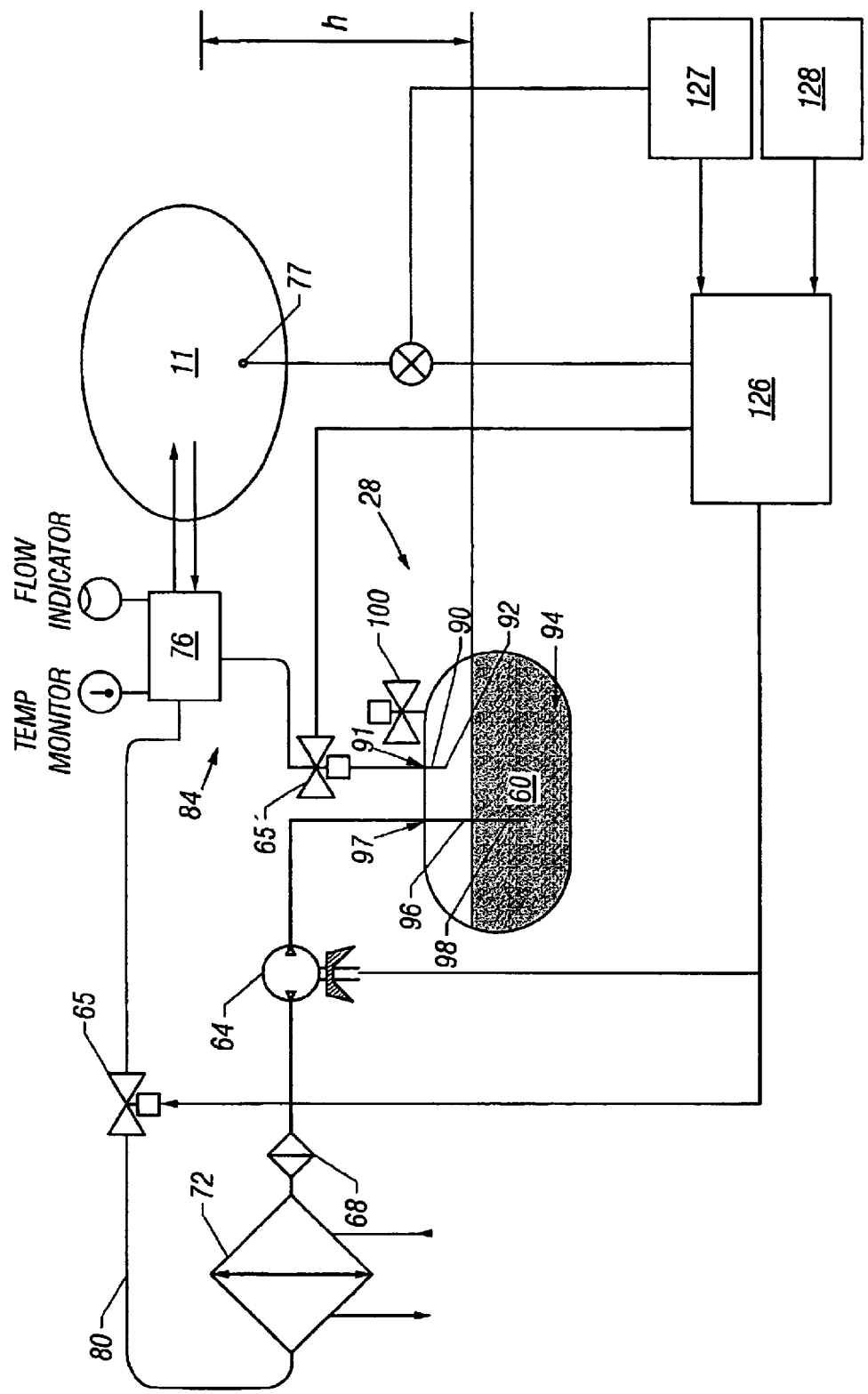
FIG. 2 is a schematic illustration of the circulation set depicted in FIG. 1, showing in particular the flow of the working fluid.

Referring to FIG. 9, one embodiment of a catheter shaft is shown in cross-section. The catheter shaft 123 includes a supply lumen 106 and a return lumen 108. A lumen 122 is also shown for providing a space through which to deliver cabling to pressure monitor 77; however, cabling for pressure monitor 77 may also be provided through a microcatheter or capillary catheter disposed within the supply lumen 106 or the return lumen 108. A separate lumen 125 is also shown for use in inflating and deflating balloon 114. A separate lumen 125 is also shown for use in delivering various drugs. While four separate lumens are shown in FIG. 9, more or less may be provided depending on the requirements of the user. With reference to FIGS. 1 and 2, an embodiment of the circulation set 28 will now be described. The circulation set 28 may include one or more of the following: a fluid reservoir 60, a pump 64, a filter 68, a heat exchanger 72, a temperature and pressure sensor assembly 76, supply line 80, and a return line 84. The supply line 80 and return line 84 are preferably comprised of one or more pieces of tubing, connectors, etc. joining the aforementioned components of the circulation set 28. The circulation set 28 supplies, filters, circulates, and monitors the temperature and pressure of the heat transfer fluid for the catheter 24.

In one embodiment, the fluid reservoir 60 is a modified IV bag made of PVC filled with saline. Since the typical bladder volume is about 500–750 cc, the volume of the fluid reservoir 60 should be greater than about 1000 cc. In this way the entire working fluid, as well as urine produced during the procedure, can be contained within the reservoir 60. Other working fluids besides saline such as, but not limited to, isotonic solutions, Ringer solution, and the like may be used. Various other solutions may be employed, including those that act to neutralize the proteins inherent in urine. In this way, when the combination of working fluid and urine is recirculated back into the bladder, the danger of infection is minimized.

The fluid reservoir 60 is used to prime the lines 80, 84 and lumens 106 and 108 of the catheter 100. For example, the system may be primed with 0.9% saline, and then the pump speed adjusted such that the driving pressure of the working fluid (by the pump) plus the return vacuum cancel out. Then, if a higher flow rate is desired, the collection bag, reservoir 60, may simply be raised higher. The fluid reservoir 60 includes a supply or inlet tube 90 that communicates at an inlet 91 with the return line 84 outside of the reservoir 60 and communicates at an opposite end or outlet 92 with an inside 94 of the reservoir 60. The fluid reservoir 60 also includes a return or outlet tube 96 that communicates at one end with the supply line 80 outside of the reservoir 60 and communicates at an opposite end, i.e., at an inlet 98, with the inside 94 of the reservoir 60.

The reservoir 60 may typically have a pressure of about 75 mm Hg (1.4 psi), although the same may be pressurized to achieve higher pressures, e.g., 300 mm Hg (5.6 psi).

The filter 68 is preferably a 5-micron filter carried by male and female housing members. The filter 68 removes impurities from the circulating heat transfer fluid. In other embodiments of the circulation set 28, the circulation set 28 may include more than one filter 68, the circulation set 28 may include no filters 68, or the filter 68 may be a part of one or more components of the circulation set.

The heat exchanger 72, which is used to heat or chill the fluid supplied to the catheter, may be any of a variety of conventionally designed heat exchangers. As noted above, the heat exchanger 72 may employ a resistive heater, a microwave heater, a thermoelectric device, a closed-circuit temperature control system, etc.

In another embodiment, a height differential 'h' may be employed between an additional fluid reservoir, such as an elevated IV bag, and the catheter. The purpose of the pump would then be to pump the combination working fluid and urine up to the additional fluid reservoir. This has a benefit in that many physicians, such as urologists, are more comfortable reading bladder pressure as centimeters of water. For example, many urologists use, as a rule of thumb, about 10–20 centimeters of water as a safe bladder pressure. The height of the top of the water in the IV bag, referenced to the approximate height of the bladder, can then be easily visually used as a measure of bladder inflation pressure.

One difficulty with this technique may be that, to force a sufficient quantity of working fluid through a catheter of reasonable size entails placing the IV bag at a height much higher than 10–20 centimeters, limiting the locations where the technique can be employed.

The control of the speed of pump 64 may be primarily given to control circuit 126, and a primary determinant of the pump speed may be the core body temperature as determined by a temperature monitor 128. The temperature monitor 128 may be an esophageal monitor, a tympanic monitor, or any other type of temperature monitor as is known in the art with which core body temperature may be monitored. In other words, the measured patient temperature may be the primary parameter on which depends the speed of pump 64. The value of the internal bladder pressure may also be used as a safety control to ensure that a dangerous over-pressure situation never arises, as is described in more detail below.

More specifically, if $\Delta T$=Target Temperature−Core Temperature, then $\Delta T$ and the internal bladder pressure may determine the pump speed and the level of "valving" of a pinch valve 65. For example, a "span" may be defined which corresponds to a $\Delta T$ small enough that very close control by control circuit 26 must occur in order to prevent overshoot. If $\Delta T$>the span, i.e., the target temperature is relatively far from the core temperature, then the pump speed is maximized and the pinch valve 65 actuated to maintain the pressure of working fluid in the bladder 11. In this mode, the maximum amount of heating (or cooling) would occur. The pinch valve 65 is actuated to ensure that the bladder is not over-pressurized, as may be measured directly or inferred by a technique described below. If $\Delta T$ is between zero and the span, then the pump speed may be set proportional to $\Delta T$, and/or the pinch valve 65 may be regulated to maintain the pressure of the working fluid in the bladder 11. In fact, due to a lessened pump speed, the pinch valve 65 may require significant opening in order to maintain the pressure of the working fluid in the bladder 11. This is because it has been noted that the pressure of the working fluid in the bladder must be maintained in order to maintain a satisfactory heat transfer rate.

As noted above, a pressure sensor 77 may be employed to measure the pressure of the working fluid in the bladder 11. This pressure sensor 77 may be provided through a throughlumen in either the supply/inlet lumen or the return/outlet lumen, and may comprise a standard medical-grade pressure transducer. This pressure sensor 77 may be referenced to a core pressure monitor 127 (the transducer of which is not shown in FIG. 2) and both may provide signals to the control circuit 126. In particular, the measured bladder pressure may be employed, when $\Delta T$ is less than the span, to control the level of valving of pinch valve 65 in order to maintain the bladder pressure at as high a level as is safe and effective for heat transfer to occur. A typical operating pressure for safe use in the bladder has been quoted in some sources as being in the range of 0.2 to 0.3 psi. It is also noted that a typical ureter transport pressure, i.e., the maximum bladder pressure which would allow an influx of urine from the ureters, has been suggested to be about 20–60 cm $H_2O$ or about 0.28–0.85 psi. Thus, this value, if properly assessed and measured, may also be used as a maximum pressure. For example, a conservative approach may be to use the lesser of the allowed pressures as a maximum.

The pressure sensor 77 and the control circuit 126 may be designed such that if a pressure higher than a predetermined value is encountered in the bladder, the pump 64 shuts down or the valve 65 completely closes or both. Other failsafe procedures may also be employed.

The pressure sensor 77 may be referenced to an internal pressure measured at another location, such as the heart line, etc. In abdominal surgery, such a reference pressure may be neglected.

Figure 4:
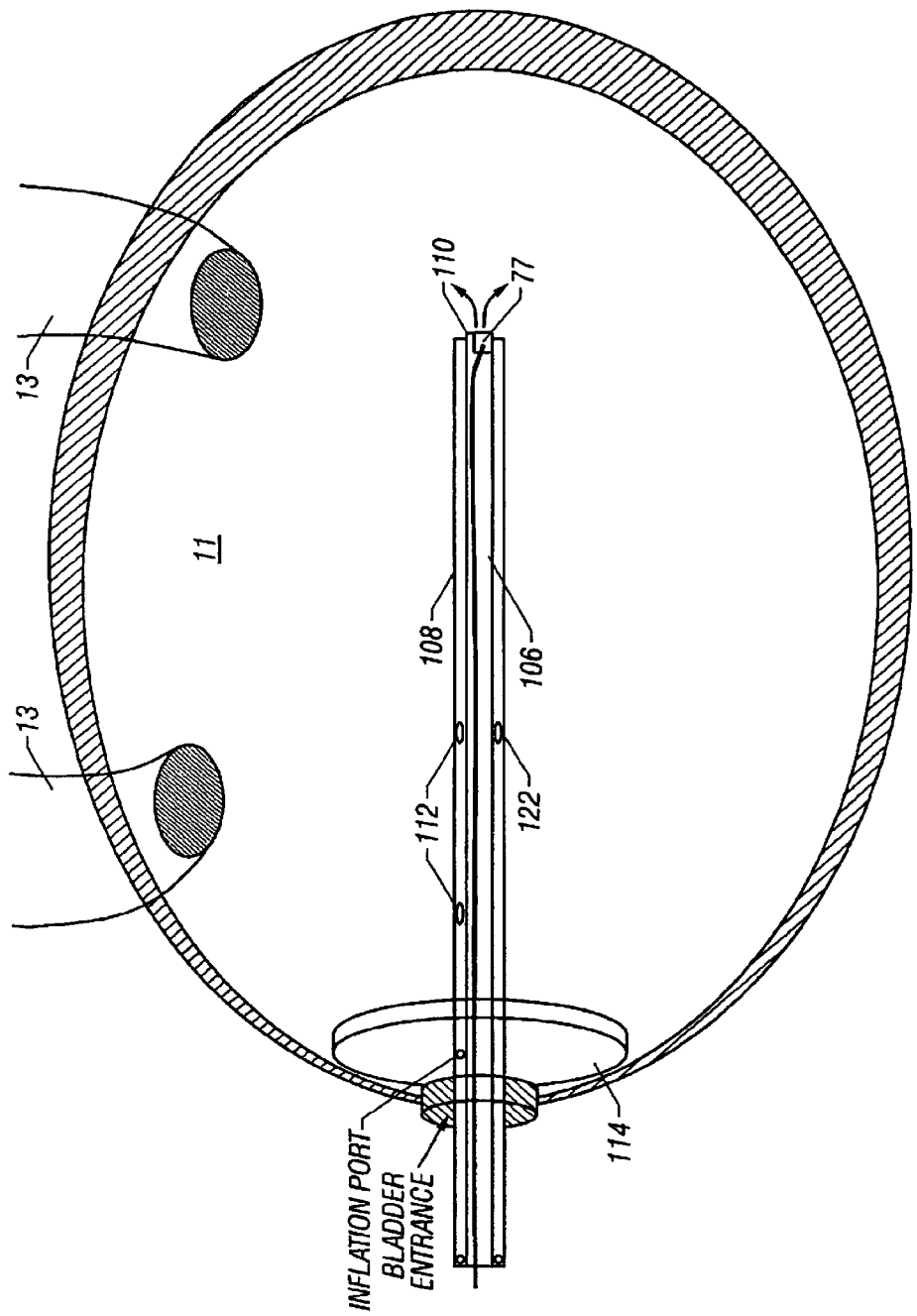
FIGS. 4–8 show different arrangements of the distal end of the catheter depicted in FIGS. 1 and 2 inserted into the bladder.
Figure 5:
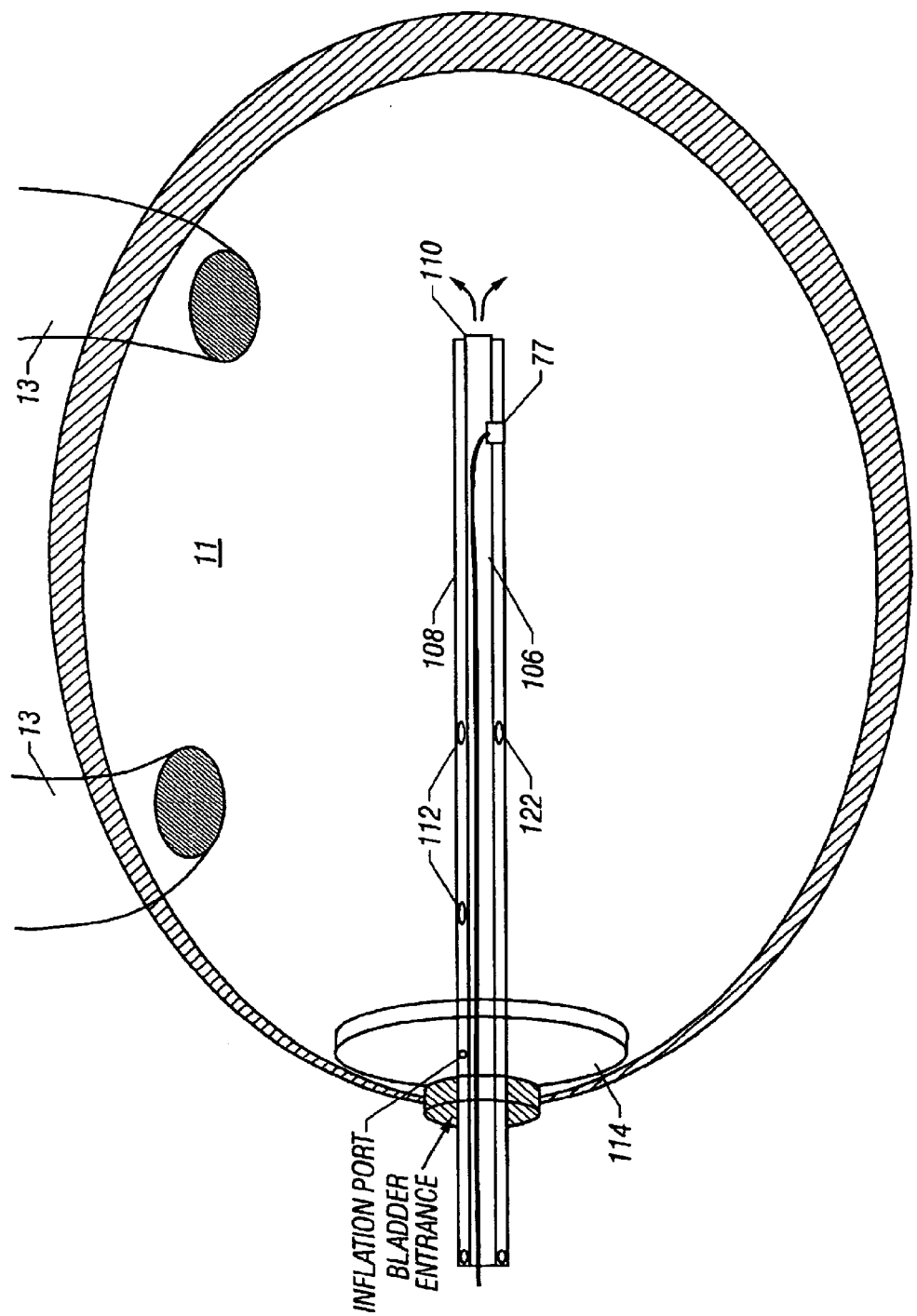
Figure 6:
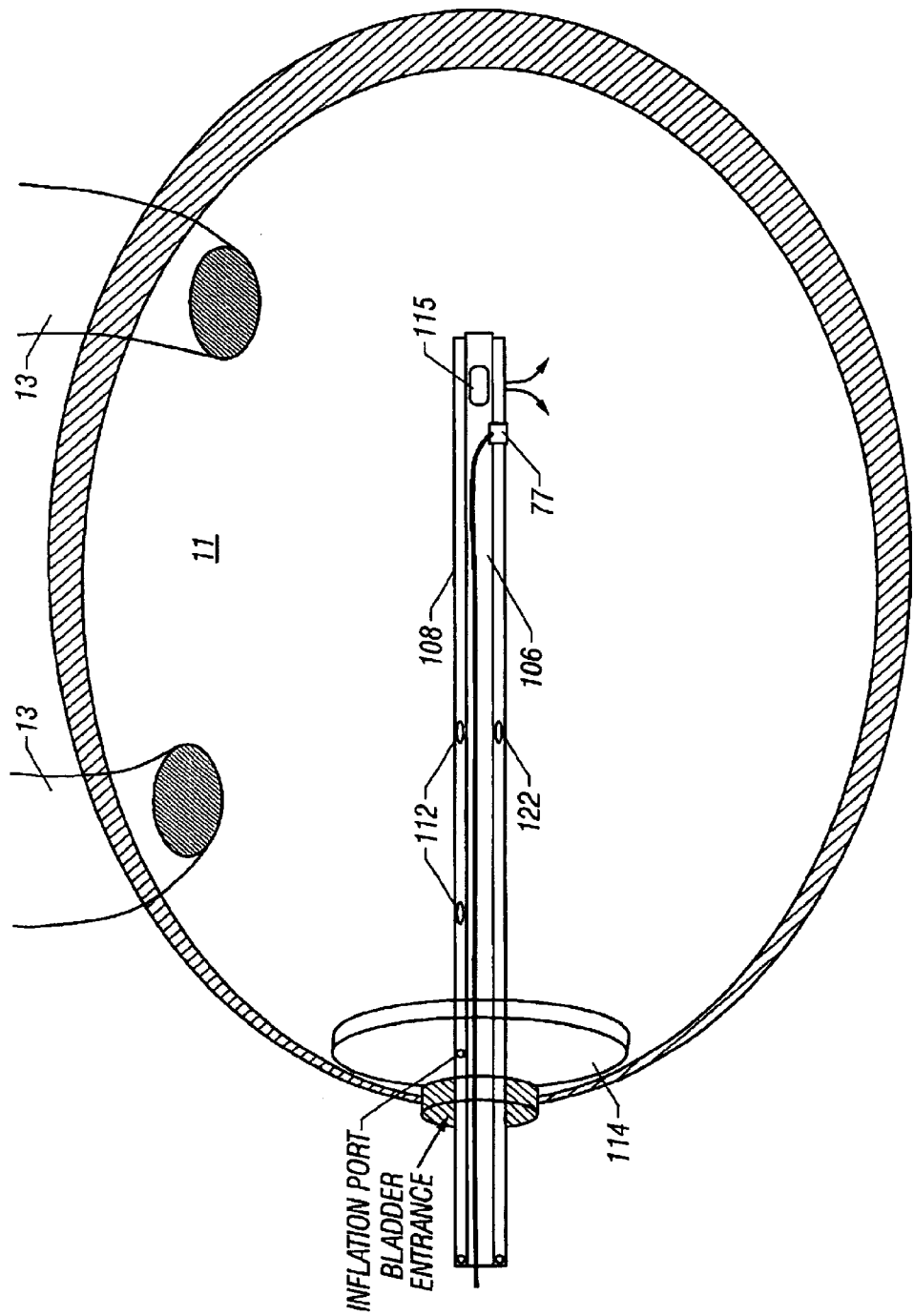
Figure 7:
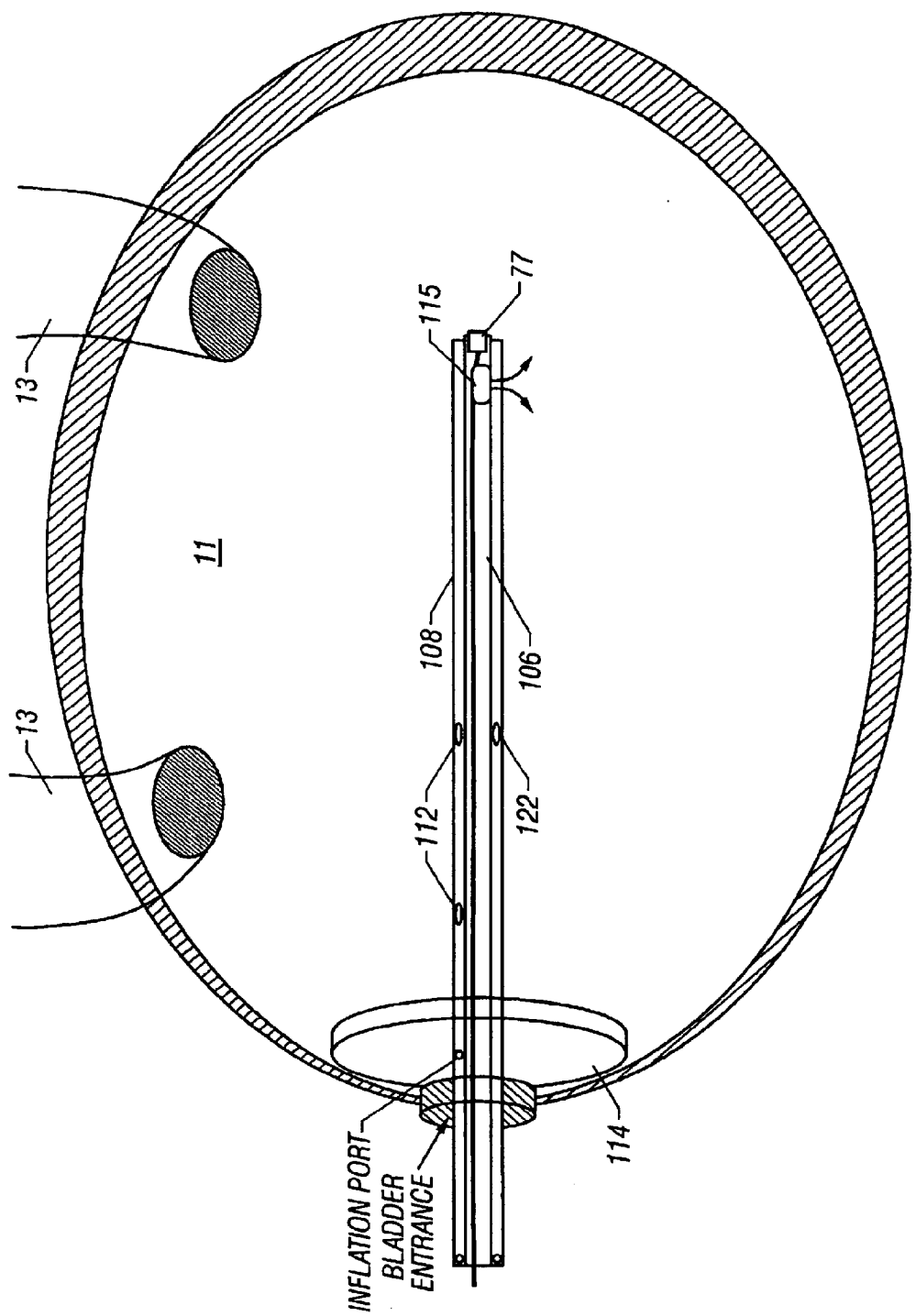
Figure 8:
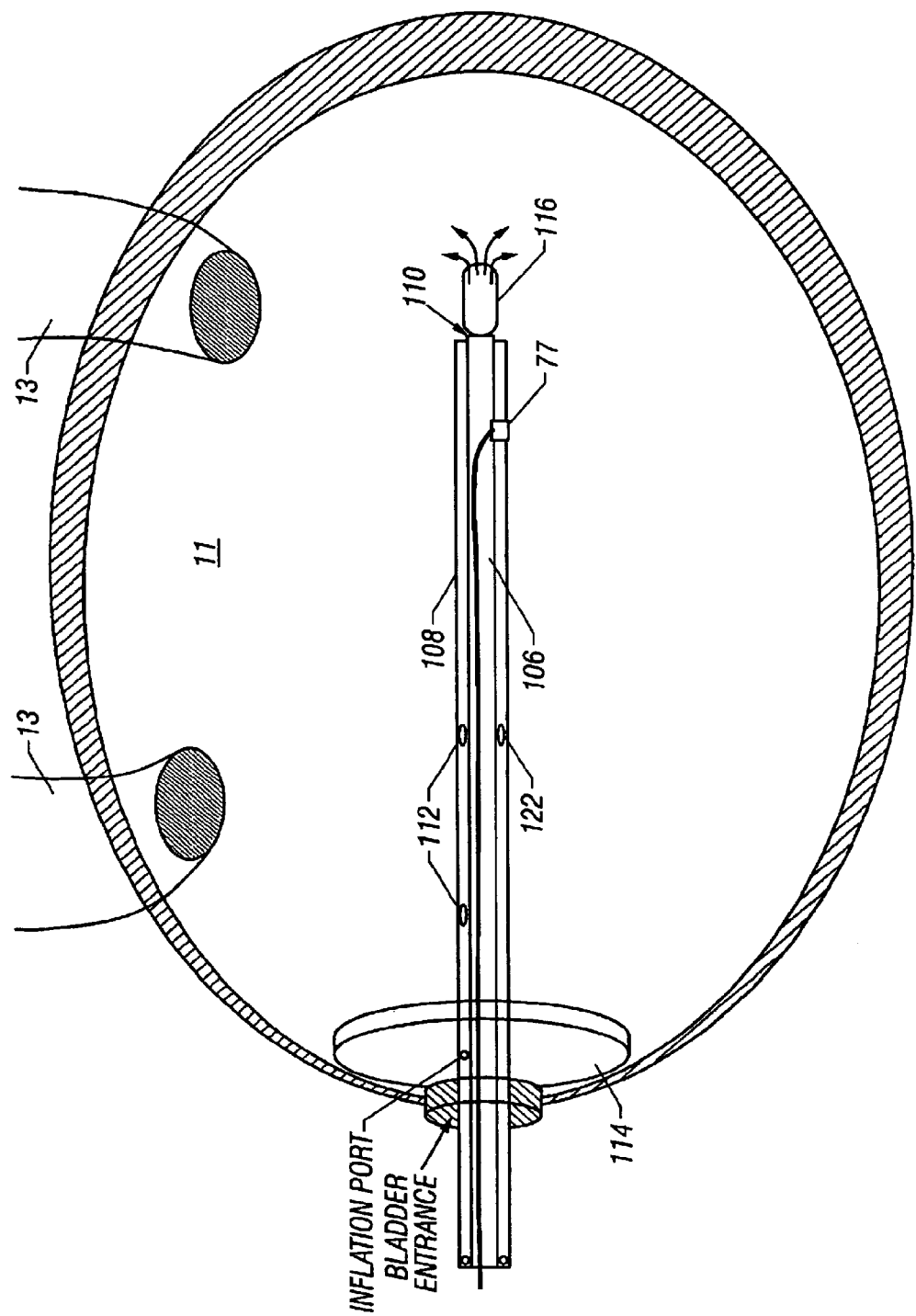

As shown in FIGS. 4–8, the pressure sensor 77 may be located in various locations with respect to the supply orifice 110. In FIG. 4, the pressure sensor 77 and the supply orifice 110 are shown in roughly the same location at the distal tip of the catheter. The pressure sensor 77 may also be proximal of the distal tip, as shown in FIG. 5. The same could be true in the case where a side supply orifice 115 is employed (FIG. 6). Alternatively, where a side supply orifice 115 is employed, the pressure sensor 77 may be located at the distal tip of the catheter (FIG. 7). If a dispersion tip 116 is employed, as is shown schematically in FIG. 8, the pressure sensor 77 may be located at the distal tip of the catheter or proximal of the distal tip of the catheter.

As noted above, the pump 64 is provided to draw the heat transfer fluid from the fluid reservoir 60 and push the fluid into the bladder 11. The flow rate of the heat transfer fluid is then determined by the speed of pump 64 as well as the state of valve 65. If the fluid column is continuous from the return ports (in the bladder) to the reservoir 60, a height h below the bladder, an effective pressure of $$p = \rho g h - K u^2$$

where K is the head loss coefficient of the drain path. In practice, maintaining a complete fluid column in the drain path results in effective draining of the bladder. To control the amount of draining, a valve 65' may be disposed in the drain path. Valve 65' may be used either in combination with valve 65 or in place thereof.

In this system, a specified flux of working fluid may be supplied to the bladder. Valve 65' can be actuated to obtained the desired bladder pressure and volume. If the supply flux is less than the drain flux, when the valve 65' is completely open, then for $p_{bladder} < p_{maximum}$, the system will not over-pressure the bladder.

The temperature and pressure sensor assembly 76 is used in one embodiment for measuring the temperature and the pressure of the heat transfer fluid in the supply line 80 before it enters the catheter 24, and measuring the temperature and the pressure of the heat transfer fluid in the return line 84, after it leaves the catheter 24. As described in more detail below, one or both of these measurements are important for determining not only the heating or cooling efficiency that can be achieved with the catheter 100, but also to ensure that the patient's bladder 11 is not irrigated at such a high rate, or subjected to such a high pressure, that renal failure occurs. The temperature and pressure sensor assembly 76 includes thermocouples and pressure transducers for respectively measuring the temperature and pressure of the fluid, and may also include associated electronics.

Signals from the temperature and pressure assembly 76 are provided to control the control circuit 126 within control unit 26 (FIGS. 1 and 2). As noted above, this information is used by control unit 26 as feedback to control the throughput of pump 64 (if included in circulation set 28), which in turn determines the flow rate of the fluid based on input parameters supplied to the control unit 26 via user input keys 40. The control unit 26 may also determine the rate of heat transferred to and from the working fluid by the heat exchanger 72.

The temperature and pressure sensor assembly 76 may include alarms that shut down the system if a dangerous situation arises. For example, a maximum safe temperature of working fluid has been quoted as being about 45° C. If this temperature were exceeded, the system may be designed to shut itself down or even turn itself off. Alternatively, a high temperature may be allowed, but only for a short predetermined period of time.

In another reference source, the mucosa in the bladder lining has been noted as being damaged after exposure to 43° C. working fluid for four hours. The "pain threshold" has been noted as 42.5° C. A "mixed fluid" temperature may be defined as that which exits the bladder, and corresponds to the temperature of fluid after the effect of mixing with existing fluid in the bladder as well as with the urine. Rather than relying for safety on a lowering of the working fluid temperature upon entering the bladder, another suitable procedure may be to set the temperature of the working fluid as high as possible, without damaging tissue, for its entry into the bladder. This would correspond to a maximum heat transfer condition. That is, the effect of mixing can only be to lower the temperature and lessen the heat transfer. Then the flow rate may be set as high as possible, again without damaging the tissue. A typical flow rate may be, e.g., about 4–5 cubic centimeters of working fluid per second. Animal experiments have shown that such flow rates may lead to about 100–120 Watts of cooling, at 2½ to 3½° C. per hour, for an animal of 40 kg. Animal experiments have also shown that such flow rates may lead to about 40 Watts of heating for an animal of 40 kg.

In a cooling regime, a suitable range of extreme low temperatures may be about 10–12° C. In particular, these temperatures would be for the temperature of the working fluid as it enters the bladder. In this regime, the temperature may be chosen to be high enough so as to not cause uric acid crystallization, etc. The circulation set 28 depicted in FIGS. 1 and 2 recirculates the heat transfer fluid so that it flows through the bladder 11 a multiple of times. In this case the heat transfer fluid would include urine that has accumulated in the bladder 11 and been conducted through the return lumen of the catheter. In other embodiments of the invention, however, the circulation set 28 may continuously replenish the supply of heat transfer fluid so that the bladder 11 is irrigated with fresh heat transfer fluid. In this case the heat transfer fluid is disposed of after being flushed from the bladder 11 by the catheter.

It is generally important during many surgical procedures to monitor the flow of urine to assess the overall physiologic balance of the patient and to ensure that renal failure does not occur. That is, if a patient is receiving an infusion of a given amount of fluid, urine monitoring should be performed to ensure that the patient is properly processing the fluid. Dangerous situations could arise if the patient were not maintaining proper hydration or if the patient were taking in fluid other than through the vasculature or the gastrointestinal system, such as the lungs, for example. This so-called "third spacing" of the fluid may lead to a hazardous situation warranting immediate intervention. In addition, renal ischemic injury such as acute tubular necrosis (ATN) can arise. If this occurs, the patient may be given the opportunity to eliminate the fluid on his or her own. That is, if the kidneys 15 (FIG. 3) fail, they may simply flush out the remaining fluid, after which no more fluid would be produced.

The typical urine output from a 70 kg patient has been measured to be about 70 ml/hour up to about a liter per day (0.6 cc/hr/kg). Of course, these numbers may vary according to the patient. Accordingly, during the procedure the volume of fluid returning from the bladder 11 in the circulation set should be monitored to ensure that it increases at the expected rate. If the volume of urine does not increase as expected, the patient may be undergoing renal failure and the procedure should be stopped so that appropriate action can be taken.

The urine output volume may be measured in a number of different ways. For example, in one embodiment of the invention in which the heat transfer fluid is recirculated, the urine output may be monitored simply by observing the change in fluid level in the fluid reservoir 60. Alternatively, or in addition thereto, the fluid level may be electronically or optically detected by a sensor so that it can be monitored by the control unit 26.

If the fluid is disposed of after being flushed from the bladder 11, control unit 26 can determine the quantity or rate of urine output simply by measuring the differential between the quantity or rate of fluid flowing into the bladder 11 and flowing out of the bladder 11 once the bladder 11 has been initially filled.

In some embodiments of the invention the control unit may automatically adjust the fluid flow rate in response to the measured urine volume. Some factors that may be considered in determining the appropriate relationship between the fluid flow rate and the urine volume will be presented below.

The volume of fluid supplied by the catheter and residing in the bladder 11 must not be so great that it upsets the physiologic balance in the bladder 11. In particular, the volume of fluid should not be so great that it exerts a pressure on the walls of the bladder 11 that prevents the flow of urine from the ureters 13 (FIG. 3) into the bladder 11. This pressure should typically be less than about 0.28–0.85 psi. One way of ensuring that this does not occur is to monitor the urine flow in the manner previously described. However, another technique may be to directly measure the pressure of the fluid in the supply line before it enters the catheter and in the return line after it leaves the catheter. It can be shown that, in the steady state, where the small urine production is ignored, that:

$$p_{BLADDER} = \frac{p_{SUPPLY} + p_{RETURN}}{2} - \frac{\Delta p_{SUPPLY}(Q) - \Delta p_{RETURN}(Q)}{2}$$

where $P_{SUPPLY}$ is the supply pressure, $P_{RETURN}$ is the return pressure, $P_{BLADDER}$ is the bladder pressure, Q is the supply and return heat flux (in the steady state), $\Delta p_{SUPPLY}(Q)$ is the pressure drop on the supply lumen, and $\Delta p_{RETURN}(Q)$ is the pressure drop on the return lumen.

In the case of identical supply and return lumens, this reduces to (as $\Delta p_{SUPPLY}(Q) = \Delta p_{RETURN}(Q)$)

$$p_{BLADDER} = \frac{p_{SUPPLY} + p_{RETURN}}{2}$$

While it may be only strictly necessary to monitor either the urine flow rate or the pressure of the fluid, in general it will be advantageous to monitor both flow rate and pressure. In this way, the occurrence of both overpressurization of the bladder 11 and renal failure can be detected. If only pressure is monitored, the occurrence of renal failure may be missed. If only flow is monitored, the bladder may become overpressurized.

The fluid may be provided to the supply lumen in a continuous, constant flow or as a pulsed flow of fluid. The pulsed flow may be a flow that is either intermittently interrupted or simply reduced in rate on an intermittent basis. A pulsed flow rate will allow urine that has accumulated in the bladder 11 to be flushed out. For example, the flow rate may be pulsed so that the bladder 11 is flushed at a regular interval, e.g., every few minutes. The present invention also contemplates more complex flow rate patterns such as periodic and aperiodic oscillatory patterns, for example. If a constant flow is used, it should be sufficiently low to ensure that the pressure in the bladder 11 is not so great that urine cannot be flushed from the bladder 11. That is, the bladder 11 pressure should be less than the pressure in the ureter 13 so that urine flow from the kidneys 15 to the bladder 11 is not prevented. Of course, in many cases it will be desirable to maintain as great a flow of fluid as possible to maximize the rate of heat exchange. If a pulsed flow is used, the pressure exerted upon the bladder 11 by each pulse may exceed the pressure that can be used in a continuous flow. However, the duration between the pulses should be sufficiently great so that urine flows out of the bladder 11 to allow drainage of the kidneys 15. The flow rate can be controlled by control unit 26 based on the information received from the temperature and/or pressure assembly 76, the values of the user input parameters received via user input keys 40, the value of pressure in the bladder measured by pressure monitor 77, or the volume or rate of urine flow out of the bladder 11.

Returning to FIGS. 3–8, which show the distal end of the catheter inserted in the bladder 11, a variety of different tips 116 may be provided over supply orifice 110 to facilitate distribution of the fluid in the bladder 11 so that the bladder 11 is thoroughly irrigated. For example, as shown in FIG. 10, tip 116a may be a diffuser that distributes the fluid in substantially all directions. The diffusing tip 116a may be formed, for example, from a porous material or an impermeable material having a series of orifices distributed over its surface.

FIG. 11 shows another tip design that employs a floating ball valve 116b. Floating ball valve 116b includes a slidable ball 117 whose movement is constrained by cage 118, which extends outward from the supply orifice 110. When fluid exits the supply orifice 110, the fluid exerts pressure on the slidable ball 117 so that the ball moves away from the orifice 110, forcing the fluid to flow out of the valve in a dispersed manner. Moreover, the floating ball valve 116b advantageously prevents substantial amounts of fluid from flowing back into the supply orifice 110 when no fluid is flowing up through the catheter. This is because when no fluid is exiting supply orifice 110, any backflow of fluid into the supply orifice 110 will cause the ball 117 to move toward, and close off, the orifice 110 as a result of the fluid's viscosity and the resulting region of reduced pressure that develops between the ball 117 and the supply orifice 110.

FIG. 12 shows yet another embodiment of the invention that employs a deflector tip 116c that has a surface 119 opposing the plane of the supply orifice 110, which deflects the fluid as it exits the orifice 110 so that it is distributed over a complete 360 region. The deflector tip 116c, which is preferably formed from a pliable material, is fixed to an insert (not shown) positioned in the supply orifice 110.

Figure 13:
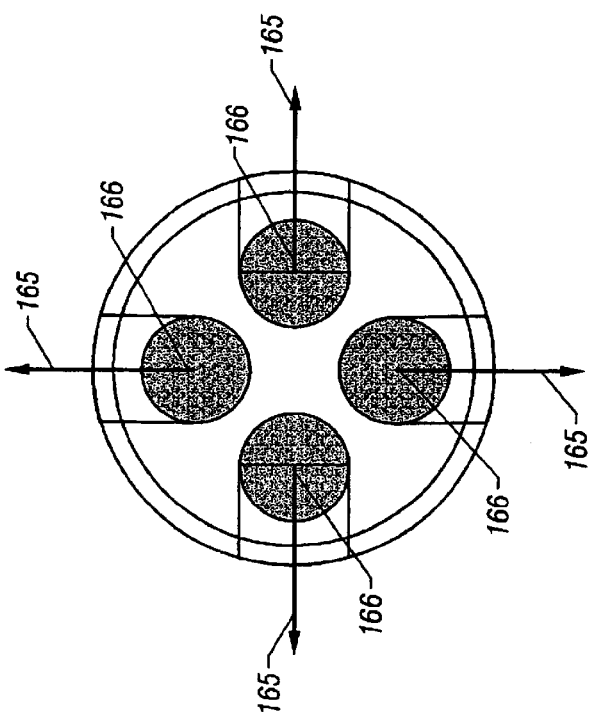
FIG. 13 shows a cross-section of the dispersion tip of FIG. 12.

FIG. 13 illustrates a cross-section of the tip of FIG. 12, and shows four roughly perpendicular fluid paths 165 emerging from four supply lumens 166. The four supply lumens 166 may all emerge themselves from supply lumen 106. In other words, supply lumen 106 may be split into four separate lumens 166 to allow four mutually perpendicular or independent flows 165 to emerge. As the insertion of a Foley-type catheter is generally uncomplicated, and can be performed by nurses or emergency personnel, embodiments of the invention may be implemented on an emergency vehicle such as an ambulance. One aspect allowing this may be inclusion in certain embodiments of a compressed gas system to cool a circulating fluid. It is again noted that in heating embodiments a simple resistive heater may be employed.

Figure 14A:
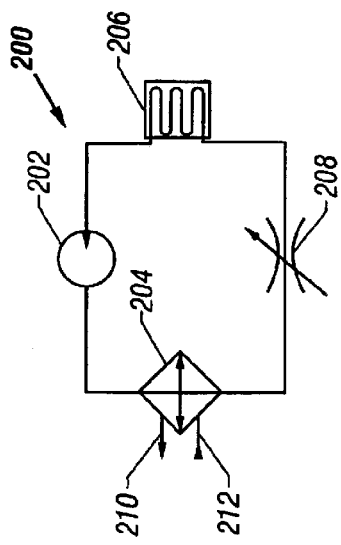
FIG. 14A shows a prior art heat exchange system.

Prior chiller units employing a closed cycle evaporative gas system were complicated, expensive, and difficult to simplify and miniaturize for use in a portable transportable system. Further, they required significant electrical power to operate. For example, referring to FIG. 14A, a prior art refrigeration system 200 is shown. Such a system is exceedingly well-known, and includes a pump 202, a heat exchanger 204, a restriction valve 208, and an apparatus 206 to exhaust heat to a temperature bath. In this system, as is known, a liquid to gas heat exchanger transfers heat from the working fluid to the cold side of an evaporative chiller.

Figure 14B:
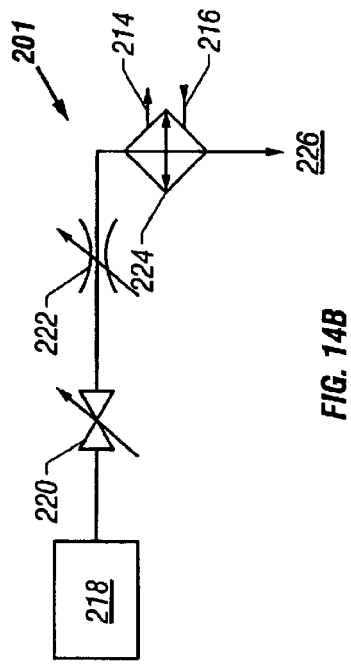
FIG. 14B shows a heat exchange system constructed in accordance with an embodiment of the invention.

A system 201 according to an embodiment of the present invention is shown in FIG. 14B. In this figure, a source of compressed gas 218 is valvably coupled via valve 220 to an optional restriction valve 222 to a heat exchanger 224. A working fluid output for, e.g., cold working fluid, is labeled by outlet 214. A working fluid input for, e.g., hot working fluid, is labeled by inlet 216. An exhaust to the environment is shown as exhaust 226.

In system 201, a compressed gas from source 218 is expanded adiabatically through a valve. The expansion results in a reduced temperature gas that absorbs heat from the working fluid in the liquid-to-gas heat exchanger 224. The heated, expanded gas is then discarded to the environment via exhaust 226. A additional temperature reduction in the expanded gas may be achieved by the phase change from the storage pressure to the expanded pressure.

Gases which may be useful in embodiments of the invention employing adiabatic expansion include nitrogen, carbon dioxide, etc. Gases which may be useful in embodiments of the invention employing adiabatic expansion with a phase change include nitrous oxide.

Of course, it should be noted that the above portable heat exchange system may be employed not only in the above bladder cooling embodiment but may also be employed as a heat exchange system for various other heat exchange catheters, including that disclosed in U.S. Pat. No. 6,096,068, incorporated above by reference in its entirety, or that disclosed in U.S. application Ser. No. 09/373,112, also incorporated by reference in its entirety.

While the invention herein disclosed is capable of obtaining the objects hereinbefore stated, it is to be understood that this disclosure is merely illustrative of the presently preferred embodiments of the invention and that no limitations are intended other than as described in the appended claims. For example, the invention can be used in a wide variety of settings, e.g., in the applications of general surgery, and in particular lengthy surgeries, orthopedic and back surgery, liver transplants, etc.

What is claimed is:

1. A catheter, comprising:
   a manifold having a proximal end with at least first and second input ports and a distal end with at least first and second output ports;
   at least first and second flexible tubes defining a supply lumen and a return lumen, respectively, said first and second flexible tubes having proximal ends removably connectable to the output ports of the manifold and having distal ends with a supply and return orifice, respectively; and
   a dispersing element associated with the supply orifice for dispersing fluid exiting the supply orifice into a portion of the body.

2. The catheter of claim 1, wherein said dispersing element is a diffusing element.

3. The catheter of claim 1, wherein said dispersing element is a floating ball valve.

4. The catheter of claim 1, wherein said dispersing element is a deflecting element.

5. The catheter of claim 1, wherein said return orifice is spatially separated from said supply orifice.

6. The catheter of claim 5, wherein said spatial separation between said supply and return orifices is sufficient to prevent a substantial flow of fluid directly from said supply orifice to said return orifice.

7. The catheter of claim 1, further comprising an inflatable balloon for maintaining an operative position of said tubes when inserted into a patient.

8. The catheter of claim 1, wherein said first and second flexible tubes are concentrically oriented with respect to one another.

9. A Foley catheter for heating or cooling at least a selected portion of a body, comprising:
   a catheter for irrigating and evacuating the bladder with a heated or chilled fluid, the catheter including:
   a manifold having a proximal end with at least first and second input ports and a distal end with at least first and second output ports;
   at least first and second flexible tubes defining a supply lumen and a return lumen, respectively, said first and second flexible tubes having proximal ends removably connectable to the output ports of the manifold and having distal ends with a supply and return orifice, respectively;
   means, coupled to the catheter, for controlling at least one measurable parameter of the fluid irrigating the bladder; and
   means for monitoring at least one parameter selected from the group consisting of: the at least one measurable parameter of fluid flowing out of the bladder while it is being irrigated, a core temperature of the body, and a pressure of the combined heated or chilled fluid and urine in the bladder.

10. The catheter of claim 9, further comprising an inflatable balloon coupled to said catheter for maintaining an operative position of said catheter when inserted into a patient.

11. The catheter of claim 9, wherein the means for monitoring the core temperature of the body is an esophageal temperature probe.

12. The catheter of claim 9, wherein the means for monitoring the core temperature of the body is a tympanic temperature probe.

13. The catheter of claim 9, wherein the means for monitoring the pressure of the bladder is a pressure transducer mounted adjacent the distal tip of the catheter.

14. The catheter of claim 9, wherein the at least one measurable parameter of fluid flowing out of the bladder is the output of urine.

15. The catheter of claim 9, further comprising a sensor for measuring the output of urine.

16. The catheter of claim 15, wherein the sensor is an optical sensor.

* * * * *